US006905456B1

(12) United States Patent
Brunner et al.

(10) Patent No.: US 6,905,456 B1
(45) Date of Patent: Jun. 14, 2005

(54) INTERMITTENT COMPRESSION DEVICE

(75) Inventors: Hans R. Brunner, Lausanne (CH); Daniel Hayoz, Villars-sur-Glane (CH); Beat Steffen, Hasle Rüegsau (CH); Ueli Haueter, Grosshöchstetten (CH); Andreas Schaer, Bäriswil (CH)

(73) Assignee: B.M.R.A. Corporation B.V., Rotterdam (NL)

( * ) Notice: Subject to any disclaimer, the term of this patent is extended or adjusted under 35 U.S.C. 154(b) by 0 days.

(21) Appl. No.: 09/720,300

(22) PCT Filed: Jun. 25, 1999

(86) PCT No.: PCT/EP99/04439

§ 371 (c)(1), (2), (4) Date: Apr. 9, 2001

(87) PCT Pub. No.: WO00/00153

PCT Pub. Date: Jan. 6, 2000

(30) Foreign Application Priority Data

Jun. 26, 1998 (DE) ........................................ 198 28 588

(51) Int. Cl.[7] ................................................ A61M 1/10

(52) U.S. Cl. ......................... 600/16; 606/202; 601/151; 601/152

(58) Field of Search ............................ 600/16, 17, 490; 601/148–152; 606/201, 202

(56) References Cited

U.S. PATENT DOCUMENTS

| | | | | | |
|---|---|---|---|---|---|
| 3,552,381 A | * | 1/1971 | Burns et al. | ............... | 128/2.05 |
| 3,752,147 A | * | 8/1973 | Castro et al. | ............... | 600/499 |
| 4,614,180 A | | 9/1986 | Gardmer et al. | | |
| 4,862,895 A | * | 9/1989 | Yamasawa et al. | ......... | 128/680 |
| 4,928,701 A | * | 5/1990 | Harada et al. | .............. | 128/677 |
| 5,634,889 A | * | 6/1997 | Gardner et al. | ............. | 601/151 |
| 5,649,954 A | | 7/1997 | McEwen | | |
| 5,746,213 A | | 5/1998 | Marks | | |
| 6,152,881 A | * | 11/2000 | Raines et al. | ............... | 600/507 |
| 6,478,757 B1 | * | 11/2002 | Barak | ......................... | 601/151 |
| 6,494,852 B1 | * | 12/2002 | Barak et al. | ................ | 601/151 |
| 6,547,741 B2 | * | 4/2003 | Mori et al. | ................. | 600/490 |

* cited by examiner

*Primary Examiner*—Jeffrey R. Jastrzab
*Assistant Examiner*—Frances P. Oropeza
(74) *Attorney, Agent, or Firm*—RatnerPrestia

(57) ABSTRACT

A device for intermittent compression of human extremities such as, for instance, the region of the calves, to assist the return of body fluid in the direction of the heart. The device comprises a cuff and a pressure generator, which intermittently pressurizes the cuff, the cuff comprising in the direction of return a width of maximally 25 centimeters. The device further comprises a pressure generator that can be secured directly to the cuff or secured to the body or to clothing. This highly compact, handy configuration enables mobile application of the device in every-day situations to assist physical well-being.

27 Claims, 5 Drawing Sheets

INTERMITTENT COMPRESSION DEVICE

FIELD OF THE INVENTION

The present invention relates to a device for intermittent compression of human extremities, which is suitable for use as a portable device in every-day situations.

BACKGROUND OF THE INVENTION

For the treatment or therapy of venous diseases or disorders, devices for intermittent compression of human body extremities find application. For this purpose, a pressure, having an effect on the extremity to be treated, is built up and reduced intermittently, i.e. with interruptions, by means of a cuff applied around the extremity to be treated. The extremity to be treated is usually totally accommodated in a large-volume single-chamber system, which is subsequently rhythmically pressurized. One such system is known from DE 704 510. Devices used nowadays are based on the multi-chamber principle, in which several cuff chambers are pressurized along the extremity to be treated in sequence distally to proximally to assist the return flow of body fluid in the direction of the heart. Configuring a multi-chamber system such that the return flow is assisted by a continuous pressure wave guided along the extremity is likewise known.

Known from EP 0 329 470 A2 is a portable pump device for a multi-chamber system. To pressurize the cuff chambers in sequence in a simple manner, a compression chamber with outlets is proposed, the number of which corresponds to the number of cuff chambers, the same number of valves being actuated in sequence in the compression chamber by means of a camshaft.

SUMMARY OF THE INVENTION

An objective of the present invention is to provide a device for intermittent compression of human extremities, which is simple to handle and inexpensive to buy, maintain, and operate.

A device according to the invention can be used in every-day situations to promote physical well-being, in particular to assist thrombosis prophylaxis, to assist the return flow of lymphatic fluid, to reduce stress, as well as or massage and quite generally to promote physical well-being.

The invention relates to a device for intermittent compression, comprising a cuff to be applied to an extremity and a pressure generator for pressurizing the cuff.

The invention is based on the discovery, made in a series of medical tests, that an intermittent compression, even on comparatively small regions of the body, has a surprisingly beneficial effect on the human organism, and assists, for example, thrombosis prophylaxis. It is on the basis of this finding that, in accordance with the invention, the cuff in the direction of the return flow of body fluid, i.e. distally to proximally, comprises a width of not more than 25 cm, preferably a width of at least 5 cm, preferably at least 8 cm and maximally 20 cm, preferably maximally 18 cm.

This amazingly simple device is excellently suited for do-it-yourself treatment without requiring a therapeutic application or even a prescription from a physician. It can e applied by a few simple movements and be started with no help from others. Supervision by medically trained personnel or admission to hospital is not required.

Preferably, the cuff, of the kind used for measuring blood pressure, is applied to the extremity to be treated and, subsequently, suitably tightened by means of a fastener. A pump is used in one embodiment as the pressure generator, preferably a compressed air generator, although a compressed fluid reservoir, for instance a compressed fluid pot, may also be used. The pressure generator, including a power supply, which might belong thereto, is preferably directly applied to the cuff; in a likewise preferred embodiment, it may be secured to a suitable location on the clothing or the body, for example, to a belt or to the stomach, and be connected to the cuff via a connection conduit. For releasably connecting the pressure generator to the cuff, the conduit may have a quick-release fastener or coupling, such as, e.g., a bayonet coupling.

Due to its small dimensions, the device can be easily carried around and, thus, may be used in every-day situations, for example, in the office, when travelling by car or air, i.e. where prolonged seated periods are involved, although it is just as suitable for use during activities involving lengthy standing periods. Due to its uncomplicated assembly of only a few simple components, the device in accordance with the invention is light, simple, robust and convenient to handle, maintain and operate as well as being inexpensive to buy. The device is particularly suitable for individual use by a user, for example, the case of thrombosis prophylaxis and as a wellness-device to reduce stress.

Preferably, the cuff chamber is configured as a single-chamber system, which also includes the case that the cuff chamber is divided longitudinally and/or transversely into several segments, which, depending on the dimensions of the segment connections , are pressurized in a defined sequence or at the same time, and preferably uniformly.

Preferably, a cuff like that employed for measuring blood pressure may be used since the cuff in accordance with the invention may, thus, be a standard product, available at a reasonable price in large numbers, the expense involved in producing and operating the device in accordance with the invention is reduced. Furthermore, obtaining spare parts is very much easier should the chamber ever become leaky. A cuff of a blood pressure measuring instrument, which the user possibly already owns, may be simply used cost-effectively within the scope of the invention.

Preferably, a diaphragm pump is used as the pump, which is available in very small dimensions and inexpensively. In principle, other miniature pumps may also be used. In one preferred embodiment, the pump is powered non-system connected by means of commercially available miniature batteries, preferably by a small rechargeable battery, which further enhances mobile employment of the device in every-day situations. However a mains-operated device or a non-system connected and a mains-operated device likewise form embodiments in accordance with the invention. Advantageously, use is made of a pump having an operating voltage in the range of 2 to 9 V, an operating current between 50 and 500 mA, and an idle capacity in the range of 0.3 to 3 liters/min, preferably in the range of 0.5 to 1 liter/min, and a maximum back pressure in the range of 300 to 800 mm Hg.

In one preferred embodiment, the device comprises a pressure control means including for example, an electro-mechanical outlet valve communicating with the atmosphere to suitably control or simply limit the pressure in the cuff chamber in a predefined manner. The valve may be an integrated component of the pump. To actuate the pump and the outlet valve, a controller, for example, in the form of a microprocessor or an application-specific integrated circuit (ASIC), may be provided, which includes a timer, and is likewise powered by the power supply of the pump. The controller ensures a suitable time control for switching the pump ON/OFF and for actuating the outlet valve.

Furthermore, the pressure control means may comprise a pressure sensor, the output signal of which is fed to the controller, which signals the outlet valve to decompress as soon as a predetermined pressure is exceeded. Instead of the output signal, derived from the pressure sensor, a signal, derived from the motor current of the pump, may be alternatively used as the parameter for regulating pressure control, this signal likewise varying with increasing back pressure in the cuff chamber.

Preferably, the pressure is controlled such that the pump is ON for a short time for compression, and the outlet valve is OFF. As soon as the predefined pressure has been built up in the chamber, the pump is switched OFF and the outlet valve—after a time which may be varied—is left open until the pump is again switched ON for the next pump cycle. In this arrangement, frequency and time duration of the compression phase are preferably given with the aid of a fixed program, although a selection function may be provided for the user in order to select from several fixed programs. Thus, preferably the maximum pressure or the repetition frequency, or both, may be tailored by the user to his individual requirements within given limits either each independent of the other or in given combinations.

Preferably, the outlet valve is open in its inoperative position to thus ensure particularly safe operation of the device.

To simplify control, the outlet valve is configured purely mechanically in another embodiment, in which an integrated pressure sensor may be provided. This pressure control means comprises an outlet valve having a stopper, which, in a first position, preferably its inoperative position, releases an outlet to the atmosphere, so that the overpressure may leak from the cuff chamber to the atmosphere, and, in a second position, shuts off the outlet, so that an overpressure may build up in the cuff chamber upon operation of the pump. Pressure build-up in the cuff chamber is preferably delayed compared to the starting pressure of the pump for controlling the outlet valve. Preferably, a restrictor is provided in a flow cross-section between the pump and the cuff.

The stopper is preferably a flexible diaphragm, separating a first chamber from a second chamber, and closing or opening the outlet. The first chamber is connected to a restrictor inlet, and the second chamber to a restrictor outlet, and comprises an outlet to the atmosphere. When the pump is switched ON, the stopper is shifted, due to the faster build-up of pressure in the first chamber and the resulting pressure difference between the two chambers, as a result of which the outlet is shut off and overpressure builds up in the cuff.

Accordingly, the pressure control may merely include a simple clock which signals the pump ON/OFF in predefined time intervals.

Preferably, the chamber of the cuff is pressurized in the range of approx. 20 to 100 mm Hg, preferably in a range of 25 to 80 mm Hg, and, in particular, in the range of 40 to 60 mm Hg. Pressure builds up within 1 to 10 sec. and, preferably, is subsequently reduced quickly within 2 to 5 sec., for example, in max 5 sec., preferably, in max 3 sec. and, in particular, within max. 1 sec, the pump thereby being actuated 1 to 15 times per 5 min, and preferably 1 to 5 times per min.

To render the device particularly user-friendly, several fixed programs, selectable by means of a switch, may be provided.

Due to its simple, handy configuration, the device in accordance with the invention may be constantly carried around by the user, and may be applied whenever required, for instance, at work or when travelling, but also when at home watching TV or while sleeping. It may be used completely inconspicuously. It is this high availability that makes effective thrombosis prophylaxis possible without therapeutic assistance.

BRIEF DESCRIPTION OF THE DRAWINGS

In the following, the invention will be detailed by way of example embodiments with reference to the Figs., in which.

DETAILED DESCRIPTION OF THE INVENTION

Figure 1:
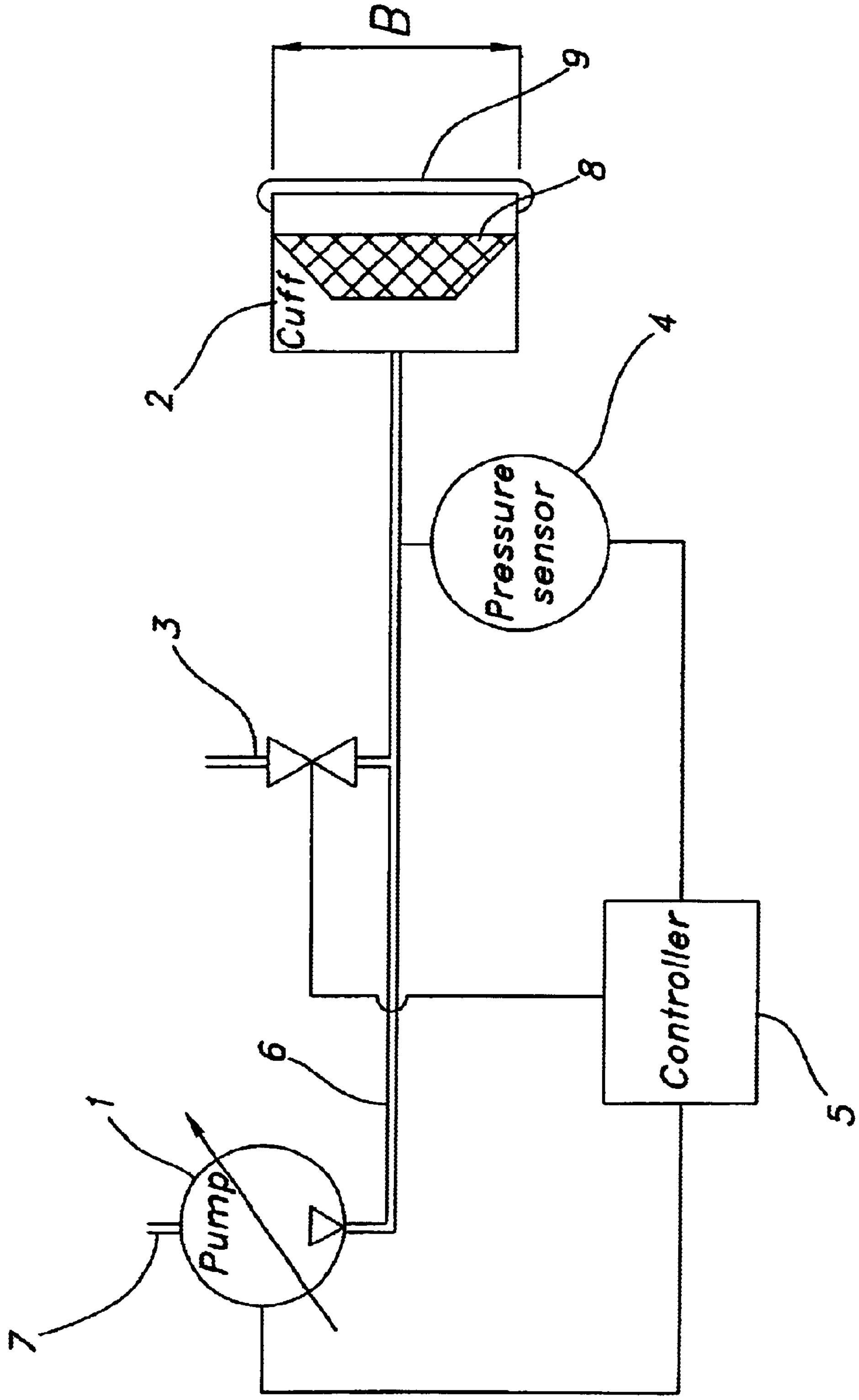
FIG. 1 shows a device in accordance with the invention.

FIG. 1 illustrates a device in accordance with the invention. It comprises a pump 1 with an inlet 7 to the atmosphere and a cuff 2, including an inflatable chamber, for application a human extremity, in particular to a region of the calves. The pump 1 is connected via a connection conduit 6 to the cuff 2, the length of which depends on the way in which the pump 1 is supported, and which should be maintained as short as possible.

The cuff 2 is configured like a cuff known for measuring blood pressure. It may have a textile covering to avoid possible skin irritation. The cuff 2 is provided with a hoop 9 for pulling through and folding over, and with a velcro fastener 8, such that it may be applied, optionally, to the left or right leg. In the unrolled condition, the portion of the cuff 2, forming the chamber, forms a simple rectangle.

The cuff 2 has an effective width B in the range of 5 to 25 cm, preferably 8 to 20 cm; in the example embodiment, it being 15 cm wide. The effective width of the cuff 2, i.e. the compressible width, is the total width of the cuff 2 in good approximation.

A controller 5, including a microprocessor and a timer, controls the pump 1 in accordance with a predefined program. A pressure control means, comprising the controller 5, comprises furthermore a controlled electromechanical outlet valve 3 for letting air escape from the cuff chamber to the atmosphere, and a pressure sensor 4 for sensing the cuff chamber pressure, expediently, also comprising a capacitive pressure sensor or a semiconductor strain gauge in a Wheatstone bridge circuit, each connected to the controller 5. The outlet valve, and also the pressure sensor, may be integrated in the cuff 2. Pressure control occurs via the controller 5. In a more complex configuration, a pressure regulator could also be provided.

The cuff 2, as such, forms the compression chamber, so that no edge seal to the wrapped surface is needed. The cuff 2 with the pump 1 and the necessary connections, thus, form a closed pressure system when the outlet is closed.

Figure 2:
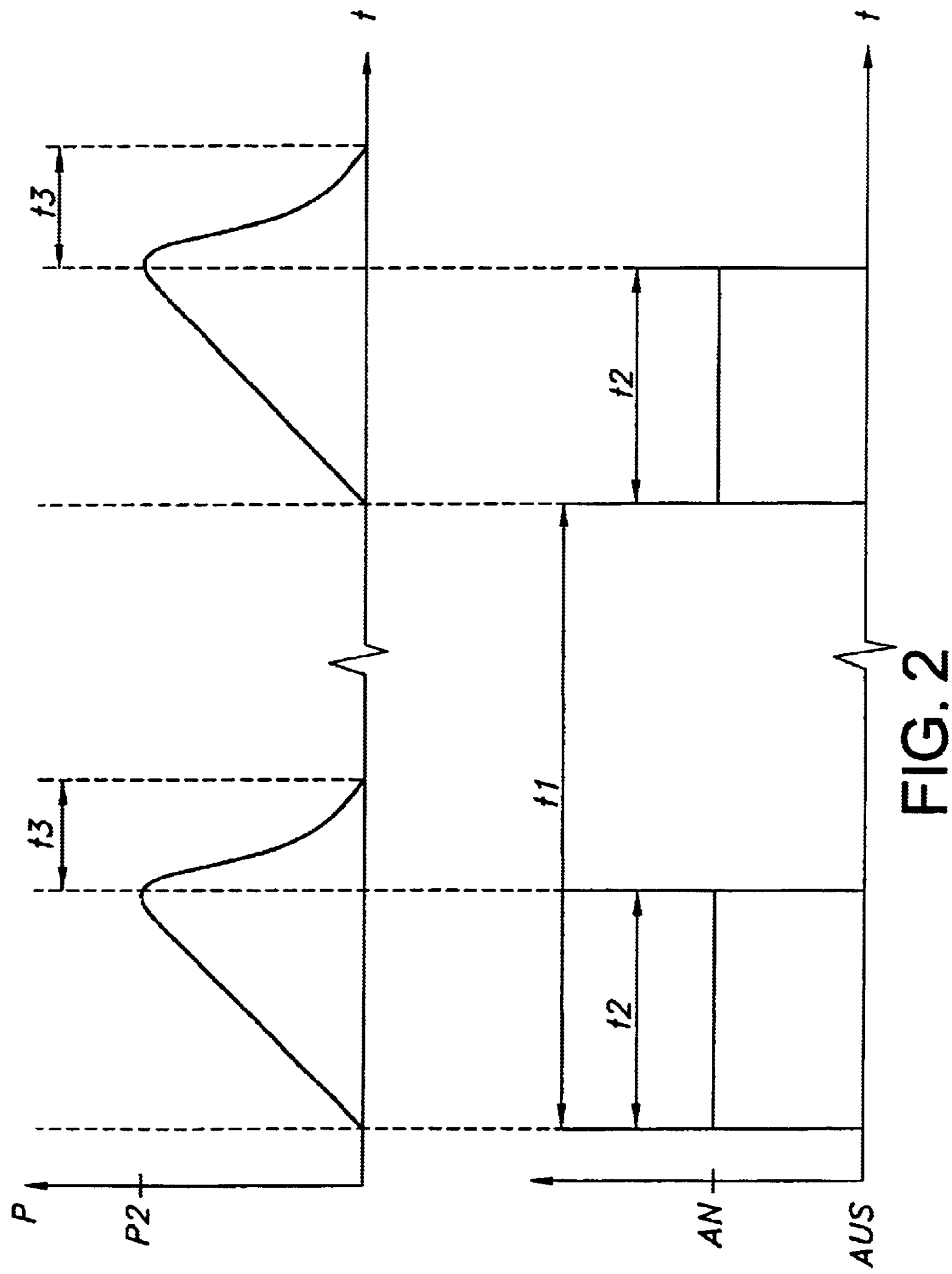
FIG. 2 is a plot of the pressure profile and the corresponding pump actions.

FIG. 2 shows, as a function of time, actuation of the pump, and the pressure existing in the inflatable chamber of the cuff.

To pressurize the inflatable chamber of the cuff 2, the pump 1, as shown in the lower half of FIG. 2, is switched ON during a time interval $t_2$. Preferably, this time interval amounts to approx. 2 to 10 sec. At this point in time, the outlet is shut off from the atmosphere via the outlet valve 3. When the pump 1 is switched OFF, the outlet valve 3 releases the outlet either instantly or after a brief delay. The release may also occur as a function of an output signal of the pressure sensor 4 or of a signal, corresponding to the size of the motor current. After the release, the overpressure in the cuff chamber reduces during the time interval $t_3$ roughly back to atmospheric pressure. Preferably, this time interval is shorter than the time interval $t_2$, which can be assured by suitably designing the flow cross-sections concerned.

Upon expiration of the time interval $t_1$, the pump 1 is reactivated so that an overpressure builds up again in the cuff chamber in accordance with the above-mentioned sequence. Preferably, this cycle is repeated one to five times per 5 min in accordance with the programming of the controller 5.

In the inoperative position of the outlet valve 3, the cuff chamber is connected to the atmosphere via the outlet valve 3, so that the outlet valve 3 is activated only during the comparatively short time interval $t_2$.

The inflatable chamber of the cuff 2 may be segmented in its length and/or width for better adaptation to the extremity. However, the chamber is configured as a whole as a single-chamber system so that a uniform pressure builds up in the several chamber segments.

The pump used is a diaphragm pump, as made, for example, by OKEN SEIKO Co., Ltd., Tokyo, Japan, in types P23B, P23E, P36B or P36C. The preferred characteristics being: voltage 2 to 7 V, current 50 to 400 mA, idle capacity 0.5 to 2 liters/min. To power, the pump is connected to a battery or rechargeable battery (nonsystem-connection operation); although, in addition, or instead, a connection may be provided to an external power supply (line operation).

Figure 3:
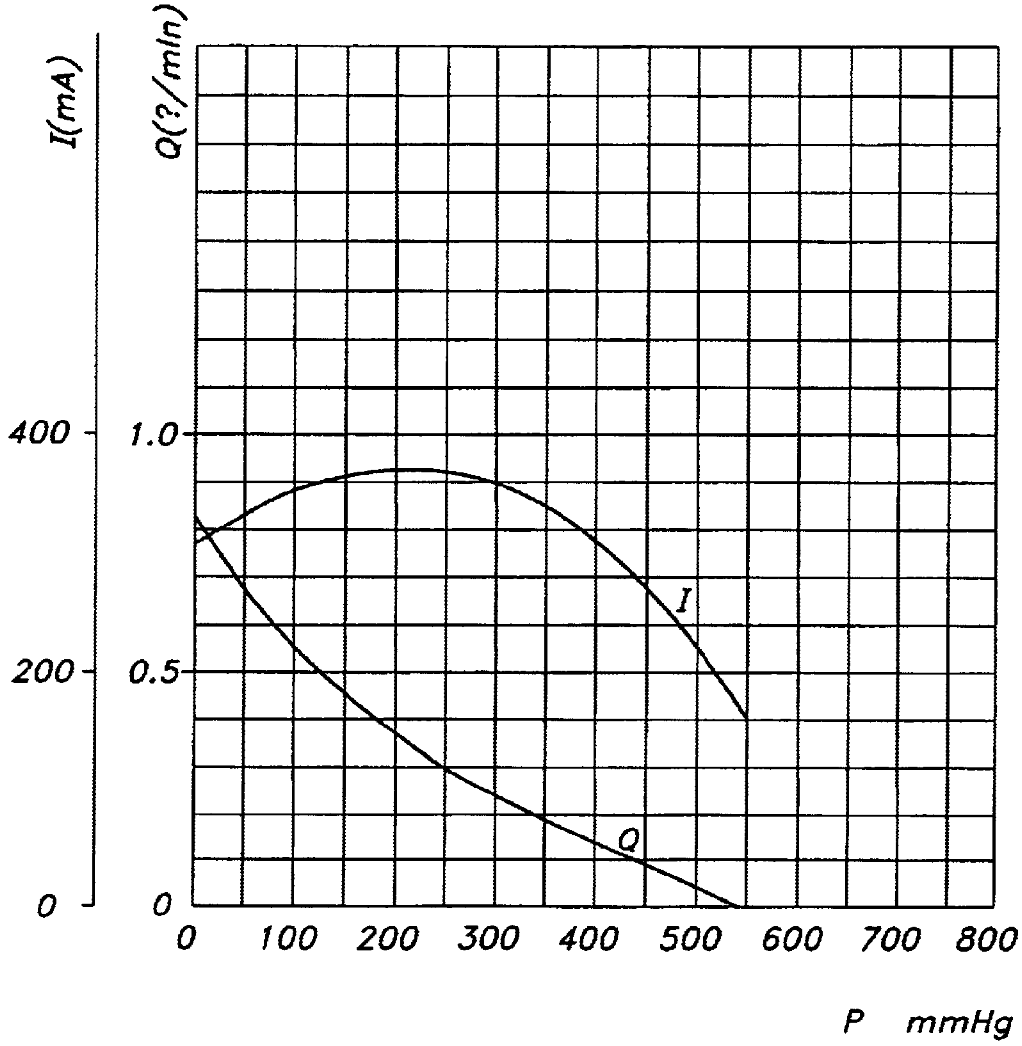
FIG. 3 is a plot illustrating pump characteristics.

FIG. 3 illustrates a plot of the characteristics of a preferred miniature pump, The max. delivery is approx. 0.8 liter/m at a back pressure P or chamber pressure of 0 mm Hg. From this maximum value, the delivery Q falls along the characteristic curve to the value zero at a back pressure P of 550 mm Hg. Maximum current consumption I occurs at a back pressure P of 200 mm Hg and runs above the working range of the pump along its characteristic curve I.

The pump, energy source and pressure control means are all accommodated in a box, which is preferably releasably secured directly to the cuff by means of a velcro fastener. In another embodiment, the pump is applied to the extremity in the vicinity of the cuff by means of an elastic band with a velcro fastener. In a further preferred embodiment, the pump is accommodated in a pouch on the outside of the cuff.

The connection conduit 6 in the example embodiment is a plastic tube, releasably or fixedly connected to the pump or cuff via a tube adapter. The connection conduit 6 may include a bayonet coupling, a velcro fastener or other suitable couplings to separate the pump and the cuff, for example, for the purpose of exchange. They may be formed by such couplings themselves.

Preferably, in the cuff chamber, an overpressure in the range of 40 to 60 mm Hg occurs. The time interval $t_1$ is in the range of approx. 1 to 3 min.

In one variant of the embodiment, the user may choose between two pressure levels and two repetition frequencies, preferably 40 or 60 mm Hg overpressure and one or five repetitions per min, the program for this being selected with the aid of a switch or pushbutton.

Figure 4:
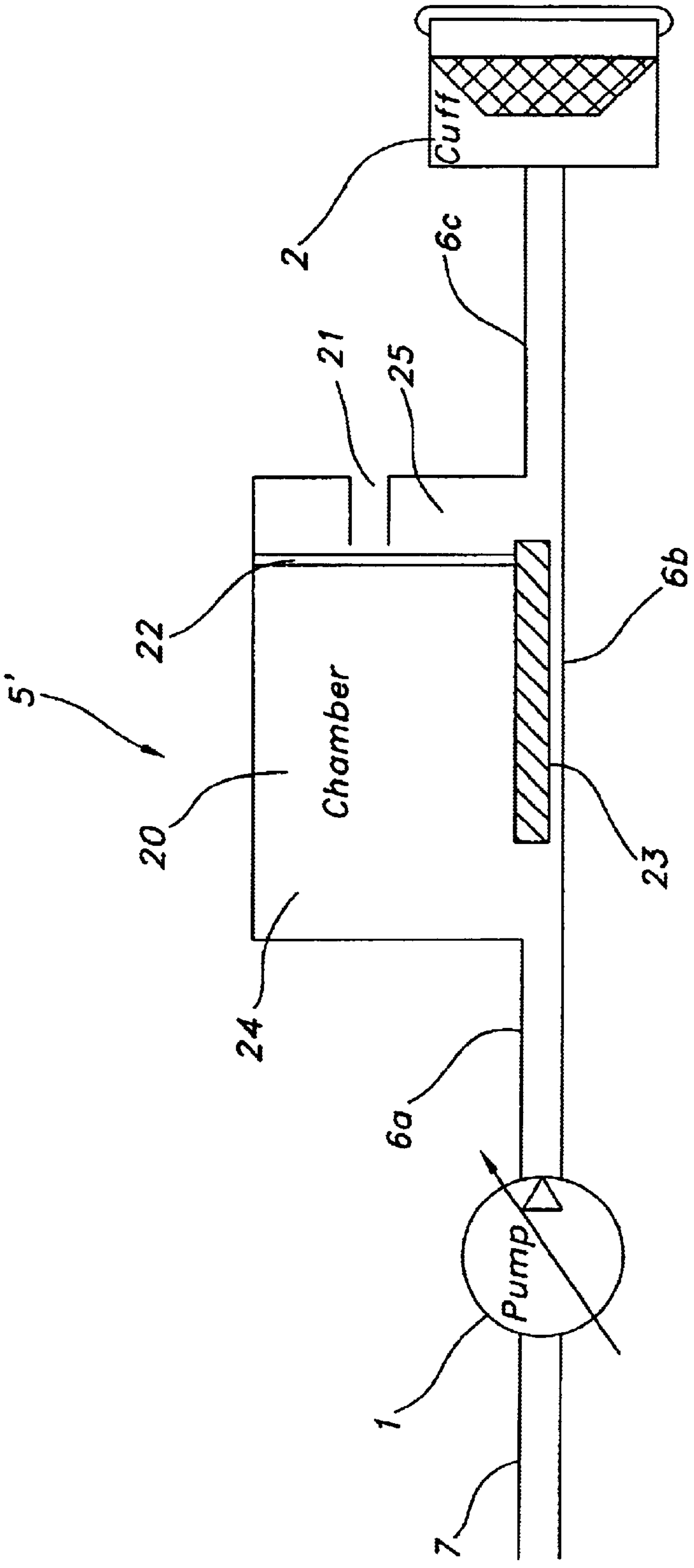
FIG. 4 shows another embodiment of the device in accordance with the invention.

FIG. 4 illustrates a further embodiment of the device in accordance with the invention, in which, instead of an electromechanical outlet valve controlled by a controller, a purely mechanical outlet valve, with a pressure sensor already integrated therein, is employed. It is to be noted that the same parts as those already described above are identified by the same reference numerals in the Figure.

A chamber 20, divided by a stopper 22 into two partial chambers 24 and 25, separated pressure-tight from each other, and circuited in parallel to the connection 6*a*, 6*b* and 6*c* between pump 1 and cuff 2, serves to control the pressure. The first partial chamber 24 communicates with the pump 1 via the connection 6*a*, and the second partial chamber 25 with the cuff 2 via the connection 6*c*. The connection 6*b*, by which also the partial chambers 24 and 25 communicate, is more constricted compared to connection 6*a*. Section 6*b* forms a restrictor due to the prescence of constrictor element 23.

The stopper 22 is configured as an elastic diaphragm of suitable thickness and elasticity, preventing cuff 2 and pump 1 short-circuiting via the partial chambers 24 and 25.

For intermittent pressurization of the cuff, the pump 1 is controlled in accordance with the timing profile qualitatively shown in the lower half of FIG. 2. Due to the constricted flow cross-section of the connecting section 6*b*, the pressure within the partial chamber 24 builds up faster, after switching ON the pump 1, in the time interval $t_2$, than in the partial chamber 25. In the partial chamber 25, the pressure of the cuff chamber 2 prevails. Due to the resulting difference in pressure over the stopper 22, the stopper 22 is curved to the right in its first position, as shown in FIG. 4, and shuts off the outlet 21. After a pressure equalization, as regards the partial chambers 24 and 25, which is taking place with a delay via the connecting section 6*b*, is substantially totally concluded towards the end of the time interval $t_2$, the diaphragm 22 again lifts off from the outlet 21 and releases the communication to the atmosphere, so that the overpressure built up in the cuff 2 may escape once the predefined pressure level is attained. This results in the sigmoidal pressure profile in the time interval $t_3$, as shown in the upper half of the FIG. 2. The described pressure control is attained by the stopper 22 being pre-tensioned away from the outlet 21, in particular by selection of the resiliency of the stopper. Preferably, an arrangement of the stopper is used, in which the outlet 21 is released in the fitted location of the stopper.

Instead of being configured as a diaphragm, the stopper 22 may also be provided as a ball, applied to a flexible partition, the ball being mounted to shut off the outlet 21 only against the force of a spring.

To verify the effectiveness of the device in accordance with the invention, tests were carried out on a group of healthy test persons by measuring the increase in blood flow in veins of,the thigh, located near the skin, using a Doppler echo method (echo tracking) in combination with a CW Doppler method. For this purpose, the precise diameter of the vein was measured continuously at one and the same location in the body, simultaneously with measurement of the mean blood flow rate, averaged in time, in order to calculate the blood flow over a lengthy period.

Figure 5B:
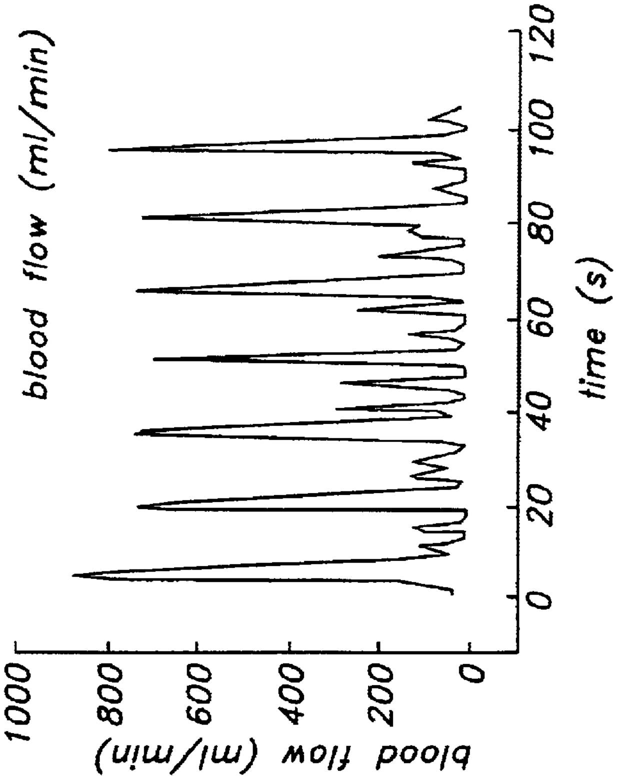
FIG. 5 is a plot (a) of two measurement curves and (b) the curve profile, calculated therefrom, as obtained in medical tests.
Figure 5A:
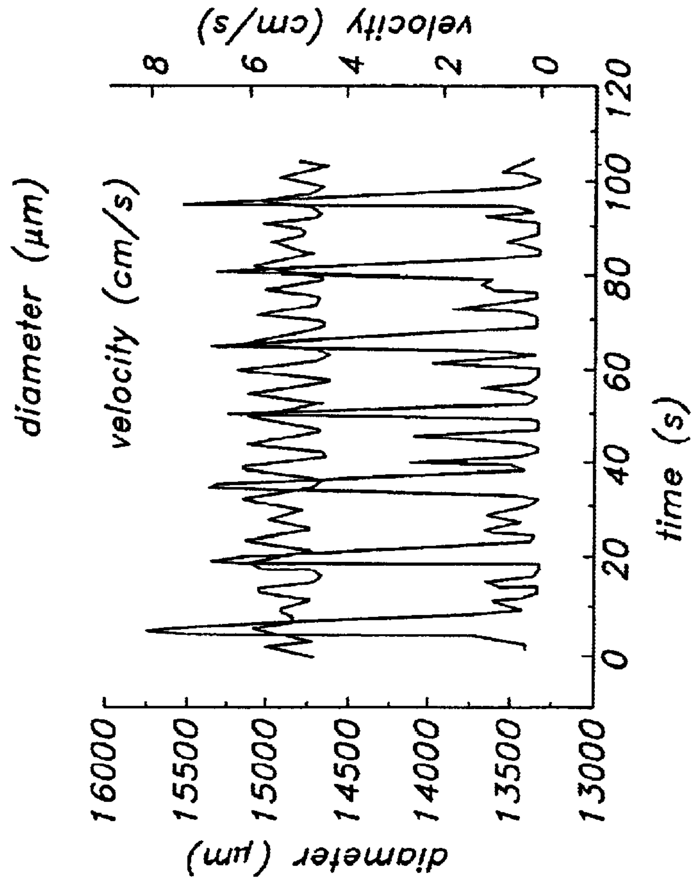

To measure the plots shown in FIG. 5, the cuff was pressurized in intervals of 20 sec., as evident from the peaks in the measurement curves. FIG. 5(*a*) plots the vein diameter measured and the flow velocity, while FIG. 5 (*b*) plots the blood flow rate calculated therefrom.

In a series of tests, the test persons were tested in both upright and seated positions. When seated, the known dilation of the veins in the region of the calves occurred, due to the elevated hydrostatic pressure. The following Table lists the test results for three different pressure amplitudes (25, 40 and 60 mm Hg) (deviations in standard deviations):

| Position | Pump Pressure (mm Hg) | Baseline | Max. Flow (change in %) | Amplitude (ml/min) |
|---|---|---|---|---|
| upright | 25 | 100% | 101% | 157 ± 21 |
| upright | 40 | 100% | 176% | 300 ± 55 |
| upright | 60 | 100% | 580% | 564 ± 88 |
| seated | 25 | 100% | 1867% | 1102 ± 246 |
| seated | 40 | 100% | 1306% | 1144 ± 258 |
| seated | 60 | 100% | 1228% | 1130 ± 183 |

The results show that, in the upright position, a pressurizing effect exists. It is surprising that a pressurizing effect is achievable with such a simple and inexpensive device. The maximum increase in blood flow was achieved at the highest pump pressure, while, in the seated position, no pressurizing effect could be observed. Accordingly, in the seated position, even a low pump pressure of, for example, 25 mm Hg is sufficient to drive on venous blood flow in the direction of the heart. The suitable pressure to be applied to the cuff and the massage effect, resulting from intermittent compression, can thus be selected by the user such that it is pleasant for him.

The effect of an intermittent compression on the volume of the calf region was also estimated, in that the test persons were seated without movement for four hours. As evident from the following Table, no increase in volume was observed, despite the test persons being totally immobile (in the following Table, deviations are given as standard deviations).

| Pump Pressure: 60 mm Hg | Volume (ml) at 8 a.m. | Volume (ml) at 12 noon | Volume Change (ml) |
|---|---|---|---|
| middle calf region, with external compression | 4076 ± 4 | 3959 ± 4 | −117 ± 4 |
| middle calf region, without external compression | 4061 ± 4 | 4138 ± 5 | +76 ± 3 |

Results show that no extravasation of fluid below the pressure level occurred. On the other hand, a slight reduction in calf volume was observed after the 4 hours of testing.

In the following, three, particularly preferred, application areas of the invention will be detailed:

A first preferred application concerns the reduction of stress and fatigue. Since, in modern professional life, tasks are mainly performed in a sitting or static, standing position, swelling may be experienced in the lower leg region (calves, feet) in the course of a working day, which affects well-being in general, and is even painful for elderly people. This condition is often treated by means of medication instead of movement. One alternative is to wear compression stockings or bandages, which, however, many concerned find unpleasant, due to the skin irritation caused by the constant skin contact pressure of the bandage.

Due to this feeling of "heavy", swollen calves, many people experience inner anxiety and stress phenomena.

In such situations, use of the device in accordance with invention presents itself, due to it being simple to use, i.e. the cuff is applied to the calf region and the intermittent compression is activated by switching on the pump or its controller. Due to the design in accordance with the invention, in particular as a handy, portable, nonsystem-connected device, it can be used in every-day situations as required, for example, at work, in the car on the way to work, when travelling, for example, in an aeroplane or train, or at home.

The intermittent compression not only stimulates the return flow of venous blood, but also the return flow of lymphatic fluid, the re-absorption of ultrafdtrate in the venous system, and the transition of high-protein fluids into an oedema through gaps in the tissue, resulting in a general detoxification of the organism and reduction of swellings.

Another preferred application is the prophylaxis of venous thrombosis. It is known that lack of movement, for instance performing tasks while sitting, or postoperative when confined to bed, may-cause blood coagulation, especially in the region of the calves or lower extremities, due to minor injuries or partially spontaneously. Blood clots block the blood vessels and, if entrained into the region of the lungs, may even result in life-threatening embolisms. It is always in locations where blood is not transported away quickly enough, but becomes blocked, that the probability of a blood coagulation becomes greater due to the change in the blood clotting behavior.

Heparin, administered in regular intervals, and the wearing of compression stockings are prescribed to counteract such risks, especially after an operation, usually for anticoagulation. However, due to its simple, inexpensive and handy configuration, the device in accordance with the invention illustrates intermittent compression as a genuine supplement, or even alternative, to such measures. By re-stimulating the venous return of blood, improved clothing behavior is re-attained, and smaller clots break up (fibrinolysis).

No counter-indication are to be anticipated for the subject matter of the invention, except in the case of persons suffering from blocked peripheral arterial blood vessels (with vascular pressure below 80 mm Hg). No other safety considerations advise against using the device in accordance with the invention, and thus it can be employed to self-treat patients, as mentioned above.

What is claimed is:

1. A device for mobile use as a readily portable device for intermittent compression of human extremities for assisting the return of body fluid in the direction of the heart, said device comprising a cuff adapted for application to an extremity for stimulating the return flow of venous blood and a miniature pressure generator for intermittent pressurization of the cuff, wherein said miniature pressure generator is secured directly to the cuff and pressurizes said cuff with an overpressure, compared to atmospheric pressure, in a range between 20 mm Hg and 100 mm Hg, and wherein said cuff has, in the direction of return flow, a width of at most 25 centimeters and is configured as a single-chamber system.

2. The device as set forth in claim 1, wherein said cuff corresponds to a cuff as used for blood pressure measurements.

3. The device as set forth in claim 1, wherein said pressure generator is a roller pump.

4. The device as set forth in claim 1 further comprising a pressure control means, which connects a cuff chamber defined by said cuff to the atmosphere when a pressure therein exceeds a predefined overpressure, compared to atmospheric pressure.

5. The device as set forth in claim 4, wherein said pressure control means comprises an outlet valve forming an overpressure outlet for said cuff, said overpressure outlet being open, except when said pressure generator pressurizes said cuff.

6. The device as set forth in claim 4, wherein said pressure control means comprises a restrictor in a conduit between said pressure generator and said cuff, and an outlet valve with a stopper, which, in a first position, releases an outlet to the atmosphere, and, in a second position, blocks said outlet, said stopper assuming these positions as a function of the difference in pressure between an inlet and an outlet of said restrictor.

7. The device as set forth in claim 1 further comprising a controller which switches said pressure generator ON/OFF, thereby pressurizing said cuff with a defined or definable pressure amplitude and a defined or definable repetition frequency.

8. The device as set forth in claim 7, wherein said controller is designed to vary at least one of said pressure amplitude and said repetition frequency.

9. The device as set forth in claim 1, wherein the overpressure of said cuff, compared to atmospheric pressure, ranges between 25 mm Hg and 80 mm Hg.

10. The device as set forth in claim 1, wherein said cuff is pressurized 1 to 10 times per minute.

11. The device as set forth in claim 1, wherein said cuff is pressurized 1 to 15 times per 5 minutes.

12. The device as set forth in claim 1 further comprising means for uncoupling said pressure generator from said cuff.

13. The device as set forth in claim 1 further comprising a hook and loop fastener for directly securing said miniature pressure generator to the cuff.

14. The device as set forth in claim 1, wherein said miniature pressure generator is accommodated in a pouch on the outside of the cuff.

15. The device as set forth in claim 9, wherein the overpressure of said cuff, compared to atmospheric pressure, ranges between 40 mm Hg and 60 mm Hg.

16. The device as set forth in claim 1, wherein the overpressure is in the range of between about 25 mm Hg to about 60 mm Hg.

17. A method for stimulating the flow of body fluid comprising the steps of:

applying a cuff to an extremity, wherein said cuff has, in the direction of return flow of venous blood, a width of at most 25 centimeters and is configured as a single-chamber system; and intermittently pressurizing said cuff by a miniature pressure generator, wherein the steps of applying said cuff to an extremity and Intermittently pressurizing said cuff stimulates the return flow of venous blood, wherein said miniature pressure generator is secured directly to the cuff and pressurizes said cuff with an overpressure, compared to atmospheric pressure, in a range between 20 mm Hg and 100 mm Hg.

18. The method as set forth in claim 17, wherein the step of intermittently pressurizing said cuff comprises a controller actuating a pressure generator to pressurize said cuff with a defined or definable pressure amplitude and a defined or definable repetition frequency.

19. The method as set forth in claim 18, wherein said controller varies at least one of said pressure amplitude and said repetition frequency.

20. The method as set forth in claim 17, wherein the step of intermittently pressurizing said cuff comprises pressurizing said cuff 1 to 10 times per minute.

21. The method as set forth in claim 17, wherein the step of intermittently pressurizing said cuff comprises pressurizing said cuff 1 to 15 times per 5 minutes.

22. The method as set forth in claim 17, wherein the overpressure is in the range of between about 25 mm Hg to about 60 mm Hg.

23. The method as set forth in claim 17, wherein the extremity is the calf muscle of a lower leg.

24. A device for mobile use as a readily portable device for intermittent compression of human extremities for assisting the return flow of body fluid in the direction of the heart, said device comprising:

a cuff adapted for application to an extremity for stimulating the return flow of venous blood, wherein said cuff has, in the direction of return flow, a width of at most 25 centimeters and is configured as a single-chamber system;

a miniature pressure generator for intermittent pressurization of said cuff, wherein said miniature pressure generator pressurizes said cuff with an overpressure, compared to atmospheric pressure, in a range between 20 mm Hg and 100 mm Hg; and an elastic band with a hook and loop fastener for securing said miniature pressure generator to a suitable location on the clothing.

25. A device for mobile use as a readily portable device for intermittent compression of human extremities for assisting the return flow of body fluid in the direction of the heart, said device comprising:

a cuff adapted for application to an extremity for stimulating the return flow of venous blood, wherein said cuff has, in the direction of return flow, a width of at most 25 centimeters and is configured as a single-chamber system;

a miniature pressure generator for intermittent pressurization of said cuff, wherein said miniature pressure generator pressurizes said cuff with an overpressure, compared to atmospheric pressure, in a range between 20 mm Hg and 100 mm Hg; and an elastic band with a hook and loop fastener for securing said miniature pressure generator to a suitable location on the body.

26. A method for stimulating the flow of body fluid comprising the steps of:

applying a cuff to an extremity, wherein said cuff has, in the direction of return flow of venous blood, a width of at most 25 centimeters and is configured as a single-chamber system; and intermittently pressurizing said cuff with a miniature pressure generator to stimulate the return flow of venous blood, wherein said miniature pressure generator pressurizes said cuff with an overpressure, compared to atmospheric pressure, in a range between 20 mm Hg and 100 mm Hg, and wherein said miniature pressure generator has an elastic band with a hook and loop fastener for securing said miniature pressure generator to a suitable location on the clothing.

27. A method for stimulating the flow of body fluid comprising the steps of:

applying a cuff to an extremity, wherein said cuff has, in the direction of return flow of venous blood, a width of at most 25 centimeters and is configured as a single-chamber system; and intermittently pressurizing said cuff with a miniature pressure generator to stimulate the return flow of venous blood, wherein said miniature pressure generator pressurizes said cuff with an overpressure, compared to atmospheric pressure, in a range between 20 mm Hg and 100 mm Hg, and wherein said miniature pressure generator has an elastic band with a hook and loop fastener for securing said miniature pressure generator to a suitable location on the body.

* * * * *